US008030485B2

(12) United States Patent
Schneider et al.

(10) Patent No.: US 8,030,485 B2
(45) Date of Patent: Oct. 4, 2011

(54) PROCESS FOR THE PREPARATION OF PULVERULENT ALKOXYCARBONYLAMINOTRIAZINE

(75) Inventors: Joerg Schneider, Wezembeek-Oppern (BE); Guenter Scherr, Ludwigshafen (DE); Rainer Erhardt, Mannheim (DE); Andreas Eichfelder, Maxdorf (DE); Martin Reif, Roemerberg (DE); Stefan Hirsch, Neustadt an der Weinstrass (DE); Georg Sieder, Bad Duerkheim (DE); Thomas Holtmann, Speyer (DE); Juergen Ciprian, Ludwigshafen (DE); Hermann Ascherl, Dirmstein (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 916 days.

(21) Appl. No.: 11/916,747

(22) PCT Filed: May 31, 2006

(86) PCT No.: PCT/EP2006/062764
§ 371 (c)(1),
(2), (4) Date: Dec. 6, 2007

(87) PCT Pub. No.: WO2006/131474
PCT Pub. Date: Dec. 14, 2006

(65) Prior Publication Data
US 2008/0207901 A1    Aug. 28, 2008

(30) Foreign Application Priority Data

Jun. 6, 2005  (DE) .......................... 10 2005 025 855

(51) Int. Cl.
*C07D 251/70* (2006.01)
*C07D 251/50* (2006.01)
*C07D 251/48* (2006.01)
*C07D 251/18* (2006.01)
(52) U.S. Cl. ........................................ 544/196; 544/200
(58) Field of Classification Search .................. 544/196
See application file for complete search history.

(56) References Cited

U.S. PATENT DOCUMENTS

| 6,512,026 | B1  | 1/2003 | Ott et al. | |
| 7,169,923 | B2* | 1/2007 | Schneider et al. | 544/196 |
| 7,371,856 | B2* | 5/2008 | Schneider et al. | 544/196 |
| 7,507,818 | B2* | 3/2009 | Schneider et al. | 544/196 |
| 7,517,474 | B2* | 4/2009 | Wagner et al. | 252/401 |
| 2004/0249149 | A1 | 12/2004 | Schneider et al. | |
| 2006/0069254 | A1 | 3/2006 | Schneider et al. | |
| 2007/0196668 | A1* | 8/2007 | Heischkel et al. | 428/423.1 |
| 2007/0208101 | A1* | 9/2007 | Heischkel et al. | 522/174 |

FOREIGN PATENT DOCUMENTS

| CN | 1575285 A | 2/2005 |
| EP | 0 624 577 A1 | 11/1994 |
| WO | WO 03/035628 A1 | 5/2003 |
| WO | WO 2004/041922 A1 | 5/2004 |
| WO | WO 2004/054990 A2 | 7/2004 |

OTHER PUBLICATIONS

Heinz Berger, et al., "Maschinen und Apparate in der chemischen Industrie", DIPL. ING.,VEB Deutscher Verlag für Grundstoffindustrie, Leipzig, S., XP-002393526, 1968, pp. 307-318 (no translation available).

"A Complete Dictionary of Chemical Engineering Machinery Equipment in China—Special Volume for Type Selection Purchase and Sale", Editorial Committee of a Complete Dictionary of Chemical Engineering Machinery Equipment in China, Chengdu Science and Technology University Press, Dec. 31, 1993, pp. 455,457,496 and 498.

"A Complete Dictionary of Chemical Engineering Machinery Equipment in China—Special Volume for Type Selection Purchase and Sale", Editorial Committee of a Complete Dictionary of Chemical Engineering Machinery Equipment in China, Chengdu Science and Technology University Press, Dec. 31, 1993, pp. 455,457,496 and 498, (Submitting English translation only, literature reference previously filed on Apr. 7, 2010).

* cited by examiner

*Primary Examiner* — Venkataraman Balasubramanian
(74) *Attorney, Agent, or Firm* — Oblon, Spivak, McClelland, Maier & Neustadt, L.L.P.

(57) ABSTRACT

The invention relates to a process for preparing free-flowing, pulverulent alkoxycarbonylaminotriazine from an alkanolic reaction mixture which is obtained in the preparation of alkoxycarbonylaminotriazines and comprises at least one alkoxycarbonylaminotriazine, at least one cyclic and/or acyclic carbonic ester, at least one $C_1$-$C_{13}$-alkanol which optionally comprises one or two oxygen atoms in the form of ether bonds and is optionally substituted by $C_1$-$C_4$-alkyl and/or hydroxyl, and also at least one alkali metal or alkaline earth metal alkoxide, with or without melamine and with or without catalyst, by atomizing and drying the reaction mixture in a spray drier.

17 Claims, No Drawings

PROCESS FOR THE PREPARATION OF PULVERULENT ALKOXYCARBONYLAMINOTRIAZINE

The invention relates to a process for preparing pulverulent alkoxycarbonylaminotriazine from an alkanolic reaction mixture which is obtained in the preparation of alkoxycarbonylaminotriazines and comprises at least one alkoxycarbonylaminotriazine, at least one cyclic and/or acyclic carbonic ester, at least one $C_1$-$C_{13}$-alkanol which optionally comprises one or two oxygen atoms in the form of ether bonds and is optionally substituted by $C_1$-$C_4$-alkyl and/or hydroxyl, and also at least one alkali metal or alkaline earth metal alkoxide, with or without melamine and with or without catalyst.

The preparation of alkoxycarbonylaminotriazines by reacting triazines, for example melamine, with carbonic esters in the presence of a base is known, for example, from EP-A 0 624 577. In this preparation, melamine is generally reacted with a carbonic ester in the presence of the parent alkanol of the carbonic ester and in the presence of an alkali metal alkoxide based on the parent alcohol of the carbonic ester as a base. For workup, a mineral acid is added to the reaction mixture for neutralization. Suitable acids mentioned are phosphoric acid, sulfuric acid and/or hydrochloric acid. The alkoxycarbonylaminotriazine is subsequently obtained by an extraction with an organic solvent and the evaporation of the solvent. Alternatively, after the addition of the acid, a solid is isolated by filtration and is then washed and dried.

WO-A 03/035628 discloses a process for preparing alkoxycarbonylaminotriazines, in which the reaction mixture is worked up by first neutralizing with a preferably aqueous acid. Suitable acids mentioned are nitric acid, sulfuric acid, phosphoric acid or mixtures thereof, but also formic acid. After the addition of the acid to the reaction mixture, an aqueous and an alkanolic phase are formed and are separated from one another. The alkanolic phase comprises the alkoxycarbonylaminotriazine. To increase the concentration of an alkoxycarbonylaminotriazine, the organic phase is concentrated after the removal of the aqueous phase.

A corresponding process for working up a reaction mixture comprising alkoxycarbonylaminotriazine is also disclosed in WO-A 2004/054990.

WO-A 2004/041922 discloses a preparation and workup process for carbamate-melamine-formaldehyde crosslinkers. In this process, the workup is likewise effected by addition of an acid, for example sulfuric acid, formic acid, oxalic acid, phosphoric acid, hydrochloric acid or mixtures thereof. The salt formed in neutralization is removed by filtration and washing with water.

It is an object of the present invention to provide a process for preparing free-flowing, pulverulent alkoxycarbonylaminotriazine from an alkanolic reaction mixture comprising alkoxycarbonylaminotriazine.

The object is achieved by a process for preparing free-flowing, pulverulent alkoxycarbonylaminotriazine from an alkanolic reaction mixture which is obtained in the preparation of alkoxycarbonylaminotriazines and comprises at least one alkoxycarbonylaminotriazine, at least one cyclic and/or acyclic carbonic ester, at least one $C_1$-$C_{13}$-alkanol which optionally comprises one or two oxygen atoms in the form of ether bonds and is optionally substituted by $C_1$-$C_4$-alkyl and/or hydroxyl, and also at least one alkali metal alkoxide or alkaline earth metal alkoxide, with or without melamine and with or without catalyst, by atomizing and drying the reaction mixture in a spray drier.

Preferred alkoxycarbonylaminotriazines are those of the general formula (I)

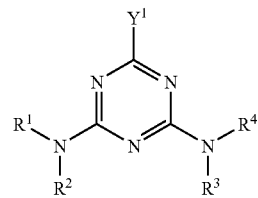

in which the symbols and indices are each defined as follows:
$Y^1$ is hydrogen, $C_1$-$C_4$-alkyl, phenyl optionally substituted by $C_1$-$C_4$-alkyl, $C_1$-$C_4$-alkoxy, or halogen, or a radical of the formula $NR^5R^6$ and $R^1$, $R^2$, $R^3$, $R^4$, $R^5$ and $R^6$ are each independently hydrogen or a radical of the formula COOX or X, or selected from the group of (—$CH_2$—O)$_l$—H, (—$CH_2$—O)$_l$—R, (—$CH_2$—O)$_k$—$CH_2$—N(Z)-Q and (—$CH_2$—O)$_k$—$CH_2$—N(Z)-Q, where k is from 0 to 10, preferably from 1 to 5, more preferably 1 or 2 and in particular 1, and l is from 1 to 10, preferably from 1 to 5, more preferably 1 or 2 and in particular 1, R is selected from the group of alkyl, cycloalkyl and alkylaryl, where the R groups comprise preferably fewer than 13 carbon atoms and R is preferably a $C_1$-$C_{13}$-alkyl and more preferably methyl or butyl, Q is a triazine radical of the general formula (II)

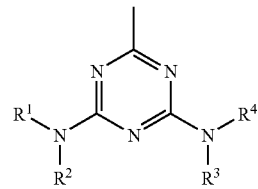

X is $C_1$-$C_{13}$-alkyl whose carbon skeleton may be interrupted by 1 or 2 nonadjacent oxygen atoms in ether function and/or substituted by hydroxyl, or is $C_3$-$C_6$-alkenyl and Z is an $R^1$, $R^2$, $R^3$, $R^4$, $R^5$ or $R^6$ radical as defined above, and at least one of the $R^1$ to $R^4$ radicals or, when $Y^1$ is $NR^5R^6$, at least one of the $R^1$ to $R^6$ radicals, is COOX.

$C_1$-$C_4$-Alkyl is, for example, methyl, ethyl, propyl, isopropyl, butyl, sec-butyl or tert-butyl.

Phenyl optionally substituted by $C_1$-$C_4$-alkyl, $C_1$-$C_4$-alkoxy or halogen is, for example, phenyl, 2-, 3- or 4-methylphenyl, 2-, 3- or 4-ethylphenyl, 2,4-dimethylphenyl, 2-, 3- or 4-methoxyphenyl, 2-, 3- or 4-ethoxyphenyl, 2,4-dimethoxyphenyl, 2-, 3- or 4-fluorophenyl or 2-, 3- or 4-chlorophenyl.

$C_1$-$C_{13}$-Alkyl whose carbon skeleton may be interrupted by 1 or 2 nonadjacent oxygen atoms in ether function and/or substituted by hydroxyl is, for example, pentyl, isopentyl, neopentyl, tert-pentyl, hexyl, 2-methylpentyl, heptyl, octyl, 2-ethylhexyl, isooctyl, nonyl, isononyl, decyl, isodecyl, undecyl, dodecyl, tridecyl, isotridecyl, 2-methoxyethyl, 2-ethoxyethyl, 2-propoxyethyl, 2-butoxyethyl, 2- or 3-methoxypropyl, 2- or 3-ethoxypropyl, 2- or 3-propoxypropyl, 2- or 4-methoxybutyl, 2- or 4-ethoxybutyl, 3,6-dioxaheptyl, 3,6-dioxaoctyl, 3,7-dioxaoctyl, 4,7-dioxaoctyl, 2- or 3-butoxypropyl, 2- or 4-butoxybutyl, 2-hydroxyethyl, 2- or 3-hydroxypropyl, 2- or 4-hydroxybutyl, 3-hydroxybut-2-yl. (The above names isooctyl, isononyl, isodecyl and isotridecyl are trivial names and stem from the alcohols obtained by the oxo process—cf. Ullmann's Encyclopedia of Industrial Chemistry, 5th Edition, Vol. A1, pages 290 to 293, and also Vol. A10, pages 284 and 285).

$C_3$-$C_6$-Alkenyl is, for example, allyl, methallyl, ethallyl, 2-, 3- or 4-penten-1-yl or 2-, 3-, 4- or 5-hexen-1-yl.

$C_1$-$C_{13}$-Alkanol which optionally comprises one or two nonadjacent oxygen atoms in the form of ether bonds and is optionally substituted by $C_1$-$C_4$-alkyl and/or hydroxyl is, for example, methanol, ethanol, propanol, isopropanol, butanol, isobutanol, sec-butanol, tert-butanol, pentanol, isopentanol, neopentanol, tert-pentanol, hexanol, 2-methylpentanol, heptanol, octanol, 2-ethylhexanol, isooctanol, nonanol, isononanol, decanol, isodecanol, undecanol, dodecanol, tridecanol, isotridecanol, 2-methoxyethanol, 2-ethoxyethanol, 2-propoxyethanol, 2-butoxyethanol, 2- or 3-methoxypropanol, 2- or 3-ethoxypropanol, 2- or 3-propoxypropanol, 2- or 4-methoxybutanol, 2- or 4-ethoxybutanol, 3,6-dioxaheptanol, 3,6-dioxaoctanol, 3,7-dioxaoctanol, 4,7-dioxaoctanol, 2- or 3-butoxypropanol, 2- or 4-butoxybutanol, ethane-1,2-diol, propane-1,2-diol, propane-1,3-diol, 3-oxa-5-hydroxypentanol, 3,6-dioxa-8-hydroxyoctanol, 3-oxa-5-hydroxy-2,5-dimethylpentanol or 3,6-dioxa-8-hydroxy-2,5,8-trimethyloctanol.

The $C_1$-$C_{13}$-alkanol which optionally comprises one or two nonadjacent oxygen atoms in the form of ether bonds and is optionally substituted by $C_1$-$C_4$-alkyl- and/or hydroxy is more preferably selected from ethanol, propanol, isopropanol, butanol, isobutanol, sec-butanol, tert-butanol, pentanol, isopentanol, neopentanol, tert-pentanol, hexanol, 2-methylpentanol and heptanol.

Very particular preference is given to butanol, isobutanol, sec-butanol and tert-butanol.

A cyclic carbonic ester is a carbonate of the general formula (III)

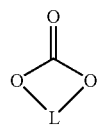

(III)

in which

L is ethylene, 1,2- or 1,3-propylene or 1,2-, 1,4-, 2,3- or 1,3-butylene.

Acyclic carbonic esters are, for example, diaryl carbonate, dialkyl carbonate, aryl alkyl carbonate and dialkenyl carbonate. The acyclic carbonic ester is preferably selected from carbonates of the general formula (IV)

(IV)

in which $Z^1$ and $Z^2$ are each independently alkyl, cycloalkyl and aryl.

The $Z^1$ and $Z^2$ radicals preferably comprise fewer than 13 carbon atoms. More preferably, $Z^1$ and $Z^2$ are a $C_1$-$C_8$-alkyl and in particular methyl or butyl.

Preferred dialkyl carbonates are dimethyl carbonate, diethyl carbonate, dipropyl carbonate, dibutyl carbonate and methyl butyl carbonate.

Preferred aryl alkyl carbonates are methyl phenyl carbonate or butyl phenyl carbonate.

Suitable diaryl carbonates are, for example, diphenyl carbonate, di(para-tolyl)carbonate, di($\alpha$-naphthyl)carbonate or di($\beta$-naphthyl)carbonate.

A preferred dialkenyl carbonate is diallyl carbonate.

Particularly preferred carbonic esters are dimethyl carbonate, diethyl carbonate, dibutyl carbonate, methyl butyl carbonate, diphenyl carbonate, propylene carbonate or mixtures thereof.

Suitable alkali metal or alkaline earth metal alkoxides are, for example, lithium, sodium, potassium, magnesium or calcium salts of the alkanols designated in detail above. The use of alkali metal methoxides, especially of sodium methoxide, is preferred. The alkali metal or alkaline earth metal alkoxide can be used either in the solid state or in dissolved or suspended form.

Preferred solvents/diluents are in this case especially the alcohols designated in detail above, alone or as a mixture with one another. However, other customary inert diluents known per se may also be used.

Catalysts which may be present in the reaction mixture are catalysts which are used to prepare the alkoxycarbonylaminotriazine. Such catalysts are, for example, phase transfer catalysts, as described in Ullmann's Encyclopedia of Industrial Chemistry, 5th Edition, Vol. A19, pages 239 to 248. Further catalysts may be metal salts or complexes, preferably oxides, chalcogenates, carbonates or halides of the alkali metals, alkaline earth metals or transition metals. Mention should be made here in particular of lithium chloride, magnesium chloride or sodium carbonate.

According to the invention, spray drying produces free-flowing, pulverulent alkoxycarbonylaminotriazine from the mixture comprising at least one alkoxy-carbonylaminotriazine.

Preference is given to effecting the spray drying in a spray drier as is known to those skilled in the art. For example, commercial spray driers with atomizer disk, one-substance nozzle or two-substance nozzle may be used for the spray drying. Depending on the design, operation can be effected in cocurrent or in countercurrent. Preference is given to using a two-substance nozzle in which the liquid phase comprising at least one alkoxycarbonylaminotriazine is atomized at ambient pressure with the aid of a nitrogen stream. The nitrogen stream has a pressure in the range from 1 to 10 bar, preferably in the range from 2 to 5 bar and more preferably in the range from 2.5 to 5 bar. The nitrogen gas is used preferably as the cycle gas.

The spray drying is carried out preferably at a temperature in the range from 50 to 250° C., preferably at a temperature of from 55 to 150° C. and more preferably at a temperature in the range from 60 to 100° C., and at ambient pressure or an elevated pressure or reduced pressure of up to +/−0.01 MPa based on ambient pressure.

The pulverulent product generated in the spray drying may be removed, for example, in a fabric filter of customary design, such as candle filters, bag filters, hose filters or other filters known to those skilled in the art, or in a cyclone. Suitable filter material for a fabric filter is, for example, polytetrafluoroethylene, silicone or polyester. Preference is given to polyester.

The nitrogen used as the cycle gas is purified preferably in a scrubber. It is possible to use any scrubber known to those skilled in the art.

In general, the reaction mixture comprising the at least one alkoxycarbonylaminotriazine is worked up before it is fed to the spray drying. For workup, the mixture is generally neutralized in a first step, ionic and/or polar components are removed, for example by ion exchange and/or by extraction, in a next step and the reaction mixture can be concentrated in a third step. The concentration can be effected either before or after the ion exchange or before or after the extraction.

In one embodiment, acid is added to the alkanolic reaction mixture for neutralization. The acid may be either in concentrated form or diluted with water. A uniform distribution of the acid in the reaction mixture is achieved by ensuring suitable mixing during the metered addition of the acid.

In a further embodiment, the alkanolic reaction mixture is introduced into an acid. The acid may be concentrated or diluted with water.

For neutralization of the reaction mixture, it is possible to use all customary and industrially available organic and inorganic acids in any concentration, preferably as 30-85% by weight aqueous solutions. Preference is given to using mineral acids whose salts have a high water solubility, such as nitric acid, sulfuric acid or phosphoric acid. A further suitable acid is formic acid. According to the invention, particular preference is given to the use of nitric acid.

To remove ionic and/or polar components, the phase comprising the at least one alkoxyaminotriazine may be fed to an ion exchange and/or an extraction before the spray drying.

The extraction is carried out with a polar extractant which is not entirely miscible with the organic phase to obtain an alkanolic phase comprising alkoxycarbonylaminotriazine and a polar phase comprising extractant with salts dissolved therein. In this context, not entirely miscible means that two phases with different composition form, and not entirely miscible is also understood to mean that the extractant and the organic phase do not mix at all. A preferred extractant is water, and particular preference is given to fully demineralized water.

Ionic components are formed, for example, by the neutralization of the alkanolic reaction mixture by addition of acid.

The neutralization of the alkanolic reaction mixture and the removal by extraction of the salts formed by the neutralization can be effected in one step or in separate process steps.

Preference is given to effecting the neutralization and the removal of the salts formed by the neutralization in two steps.

For the extraction, the apparatus known to those skilled in the art, for example mixer/settler units, columns with or without energy input or extractors which are based on the principle of centrifugal field separation, may be used. A mixer/settler unit comprises generally a mixer unit such as a stirred vessel, a mixing pump, a nozzle or a static/dynamic mixer. The mixer/settler unit further comprises a separator which is generally designed as a horizontal vessel with or without internals.

Suitable columns which can be used for the extraction are, for example, columns with structured packing or random packing, or sieve tray columns. Suitable sieve tray columns are, for example, also crossflow sieve tray columns. The random packings used may be all random packings known to those skilled in the art. Such random packings are described, for example, in Klaus Sattler, Thermische Trennverfahren [Thermal separating processes], 2nd Edition, VCH Verlagsgesellschaft mbH, Weinheim, 1995, pages 226 to 229.

Suitable structured packings are ordered or unordered packings. Such structured packings are, for example, lamellar packings, fabrics, drawn-loop knits or formed-loop knits.

The random packings, structured packings or sieve trays may be manufactured from metal or plastic. Owing to the good wetting properties of metals, preference is given to using metal as the material for the random packings, structured packings or sieve trays when the wash phase is selected as the continuous phase. Particularly suitable metals are stainless steels.

In addition to the operation of the columns with random packings, structured packings or trays with and without pulsation, it is also conceivable to use them without internals, for example as a spray column. Examples of suitable commercial extraction columns with mechanical stirrer systems are rotary disk extractors, Old-Rushton columns, Kühni extractors, stirred cell extractors, Graesser extractors. However, it is also possible to use centrifugal extractors, for example Podbielniak extractors or Lurgi-Westfalia extractors.

In the extraction to remove the salts formed by the neutralization, the wash phase comprising the polar extractant which is not entirely miscible with the organic phase may form either the continuous or the dispersed phase of the extraction. In a preferred form of the extraction, the wash phase forms the continuous phase.

In addition to the use of a single extraction apparatus, it is also possible to carry out the extraction in a plurality of apparatuses. In this case, a combination of different apparatus types may also be used. A preferred combination is formed by a mixer/settler unit and a column with random packing. In a particularly preferred embodiment, the extraction to remove salts formed by the neutralization is carried out in a column with structured packing.

In the extraction, the phase ratio of polar to organic phase is within a range from 0.1 to 2. Preference is given to a phase ratio in the range from 0.15 to 1.5, more preferably from 0.2 to 1 and in particular from 0.3 to 0.5.

When a column with structured packing is used for extraction, in a preferred embodiment, the polar phase is preferably drawn off as the extract via the bottom of the column; the raffinate, the organic phase, preferably runs off as a free overflow. The extraneous phase content, i.e. the alkanol, in the extract is preferably removed by a loop-drawn plastics knit in the bottom of the column.

When water is used as the polar extractant, the extraneous phase content, i.e. the content of undissolved water, in the raffinate after the phase separation is generally about 1 percent.

The raffinate comprises the desired product. Should the content of polar and ionic components in the raffinate be greater than the required product specification allows, it is possible in a preferred embodiment to recycle the raffinate into the feed. In this case, the raffinate may, for example, either be fed directly into the feed vessel for extraction or into a buffer vessel from which the extraction is fed.

The polar and ionic components are, for example, alkali metal or alkaline earth metal salts, alkali metal or alkaline earth metal alkoxides, acid, cyclic or acyclic mono- and/or diesters of carbonic acid, alkan(edi)ols and also polar melamine derivatives. Alkanediols are, for example glycol and propanediol; polar melamine derivatives are, for example, melamine, mono- and dialkoxycarbonylaminotriazines.

The possibility of removing mono- and dialkoxycarbonylaminotriazines from the raffinate by the extraction makes it possible to adjust, in a controlled manner, the ratios of different alkoxycarbonylaminotriazines in the raffinate.

The extraction in the column with structured packing is carried out generally as a countercurrent extraction. In a particularly preferred embodiment, this is done by feeding the polar extractant above the packing and the alkanolic reaction mixture below the packing. Within the column, the polar extractant thus flows through the packing in the direction of the column bottom and the alkanolic reaction mixture through the packing in the direction of the column top. The alkanolic reaction mixture and the polar extractant mix in the packing, and the salts present in the alkanolic reaction mixture are passed to the polar extractant and thus removed from the alkanolic reaction mixture.

The temperature at which the extraction is carried out is preferably in the range from 10 to 90° C., more preferably in the range from 15 to 50° C.

A preferred pressure at which the extraction is carried out is ambient pressure. However, it is also possible to carry out the extraction at a pressure below ambient pressure or else at an elevated pressure. When the extraction is carried out at elevated pressure, the pressure is preferably in the range from 1 to 10 bar.

Instead of the extraction, it is possible in a further process variant to remove salts from the reaction mixture by ion exchange over a cation exchanger and/or anion exchanger.

In one embodiment, the cation exchanger and/or the anion exchanger is/are present as fixed bed ion exchanger(s). Instead of the fixed bed ion exchanger, it is also possible in a further embodiment for the cation exchanger and/or the anion exchanger to be present as granule in a stirred tank.

In a preferred embodiment, the alkali metal and/or alkaline earth metal ions are removed from the alkanolic reaction mixture with a cation exchanger.

It is also possible to remove the anions of the salts with an anion exchanger. Depending on the acid used for the neutralization, anions which occur are, for example, nitrate, sulfate or phosphate ions, or else the anions of organic acids such as formic acid.

Regeneration of the laden anion exchanger is effected preferably with dilute mineral alkalis. Particularly suitable for regeneration of the anion exchanger is 5-25% sodium hydroxide solution.

The cation exchanger is regenerated preferably with dilute mineral acids. A suitable mineral acid is, for example, 5-30% hydrochloric acid.

To pass through several cycles, both the anion exchange resin and the cation exchange resin are generally pretreated with a solubilizer between organic and polar phase. To this end, the ion exchanger is rinsed with a substance which has a polarity which is between the polarity of the organic phase and of the polar phase and is preferably miscible with both phases. For example, methanol is suitable as a solubilizer when butanol is the organic phase and water is the polar phase. In addition to a regeneration of the ion exchange resin, it is also conceivable to discard the laden resin without regeneration.

Anion exchangers suitable in accordance with the invention are, for example, strongly basic anion exchange resins. Preference is given to crosslinked polystyrene resins or styrene-divinylbenzene copolymers with tertiary or quaternary amines as functional groups and $OH^-$ ions as exchange ions. Exchange ions are understood to mean the ions which are bonded to the functional groups and are exchanged for the ions to be removed from the liquid. In commercially available anion exchangers, functional groups are generally present as salts. In these anion exchangers, $Cl^-$ ions, for example, are bonded to the functional group. In order to be able to use the anion exchangers, it is in this case generally first pretreated with NaOH in order to exchange the $Cl^-$ ions for $OH^-$ ions. Suitable commercially available anion exchangers are, for example, Lewatit® MP62, Lewatit® MP64 or Lewatit® MP 600 WS from Bayer AG, or else Amberjet® 4200 CL or Ambersep® 900 OH from Rohm & Haas Co. For the removal of nitrate ions, preference is given to Ambersep® 900 OH and Lewatit® MP 600 WS, particular preference to Ambersep® 900 OH.

Suitable cation exchangers are, for example, strongly acidic cation exchanger resins based on a crosslinked polystyrene matrix or a styrene-divinylbenzene copolymer matrix and sulfonic acid as the functional group with $H^+$ ions as exchange ions. In general, the cation exchangers, just like the anion exchangers, are in their salt form when available commercially. In order to be able to use the cation exchanger, it is then generally pretreated with an acid, for example sulfuric acid, in order to exchange the cations of the salt for $H^+$ ions. Commercially available, suitable cation exchangers are, for example, Lewatit® S2528 or Lewatit® MonoPlus® S100 from Bayer AG, Amberlyst® 40 WET and Amberjet® 1500 H from Rohm & Haas Co., and also Dowex®@ N306 from Dow Chemical Co. For the removal of sodium ions, for example, preference is given to using Amberlyst® 40 WET and Amberjet® 1500 H.

The cation exchanger and the anion exchanger may be used either together as a mixture, individually or in steps or stages connected in series. Suitable combinations of suitable commercially available anion exchangers and cation exchangers are, for the removal of nitrate salts, Ambersep® 900 OH or Amberjet® 4200 as the anion exchanger and Lewatit® S2528 as the cation exchanger. Preference is given to the combination of Ambersep® 900 OH and Lewatit® S2528.

The alkanolic reaction mixture can be contacted with the cation exchanger and/or anion exchanger, for example, by adding the cation exchanger and/or anion exchanger to the reaction mixture, for example into the reactor or into a stirred vessel, or by flowing the reaction mixture through a continuous ion exchanger, in which case the ion exchanger is present, for example, as a packing in a fixed bed.

The addition of the ion exchange resin into the reaction vessel is possible especially when the alkoxycarbonylaminotriazine is prepared batchwise. In this case, preference is given to effecting both the preparation and the neutralization and the removal of the salts formed by neutralizations by ion exchange in the same vessel.

In a particularly preferred embodiment, a portion of the salts is removed from the alkanolic reaction mixture before the ion exchange by washing, extraction or filtration or combinations thereof.

The washing is effected preferably by addition of water at a temperature in the range from 10 to 70° C., preferably from 15 to 50° C., and at a pH of from 0 to 8, preferably from 2 to 5.

When an extraction is carried out after the ion exchange, it is preferably carried out as described above.

In a further step, the alkanolic reaction mixture comprising at least one alkoxycarbonylaminotriazine can be concentrated before it is sent to the spray drying.

The concentration can be effected by thermal or mechanical processes. Suitable thermal processes for the concentration are, for example, evaporation, distillation or rectification. Suitable mechanical processes are in particular membrane separation processes, for example pervaporation or permeation, and also filtration when the at least one alkoxycarbonylaminotriazine is present as a suspension. The processes for the concentration may each be employed individually or in combination. It is also possible to use any further process for concentration known to those skilled in the art. A preferred process for concentration is distillation.

The concentration of the organic phase comprising alkoxycarbonylaminotriazine by distillation can be effected continuously or batchwise.

For the continuous distillation, it is possible to use conventional continuous evaporators known to those skilled in the art. Suitable evaporators for continuous distillation are, for example, circulation evaporators such as Robert self-circulation evaporators, rapid-circulation evaporators with inclined evaporator tubes, forced-circulation evaporators with external evaporator bundles, circulation evaporators with boiling space divided into chambers, or forced-circulation evaporators with horizontal heater. Further suitable continuous evaporators are, for example, falling-film evaporators, thin-film evaporators or Kestner evaporators.

In addition, the organic phase can be concentrated by distillation in a column. The heating to evaporation temperature can be effected at the bottom of the column or in a heat exchanger disposed outside the column. Suitable columns are, for example, columns with structured packing or random packing, or tray columns. Suitable structured packings, random packings or trays are all structured packings, random packings or trays known to those skilled in the art.

Batchwise concentration by distillation can be effected, for example, in a stirred vessel. The distillation can also be carried out in the vessel in which the reaction to give alkoxycarbonylaminotriazine is carried out. Preference is given to effecting the concentration by distillation in an additional stirred vessel.

Both in the continuous and in batchwise process, the product stream comprising alkoxycarbonylaminotriazine is obtained as the liquid phase and at least one vapor stream comprising alkanol, carbonate and water. When a polar extractant different from water is used in the removal by extraction of salts formed by the neutralization, the polar extractant is present in the vapors either instead of the water or in addition.

The concentration of the organic phase comprising alkoxycarbonylaminotriazine by distillation leads, in a particularly preferred embodiment, to a product stream which comprises 45-60% by weight of alkoxycarbonylaminotriazine.

However, depending on the desired product stream, it is also possible for the distillation to afford a product stream which comprises a smaller or else a larger proportion of alkoxycarbonylaminotriazine.

In one process variant, the vapor stream obtained in the spray drying and, if appropriate, the stream which has been depleted in alkoxycarbonylaminotriazine and is obtained in the concentration of the alkoxycarbonylaminotriazine is separated distillatively into an organic phase and a polar phase. The separation may be effected continuously or batchwise.

Before the vapor stream is fed to the distillative separation, it can, in a preferred process variant, be condensed. However, it is also possible to feed the vapor in vapor form to the distillative separation.

When the distillative separation is carried out continuously, it is preferably effected in a column. Suitable columns are columns with structured packing or random packing, or tray columns. Suitable structured packings are, for example, ordered packings or drawn-loop knits or formed-loop knits. When a column with random packing is used, suitable random packings are known to those skilled in the art and are disclosed, for example, in Klaus Sattler, Thermische Trennverfahren, 2nd Edition, VCH Verlagsgesellschaft mbH, Weinheim, 1995, pages 226 to 229.

When a tray column is used, suitable trays are, for example, sieve trays, bubble-cap trays, tunnel-cap trays or crossflow trays.

The vapor stream depleted in alkoxycarbonylaminotriazine can be fed to the column either at the top, in the bottom or via a side feed. Preference is given to feeding the vapor stream via a side feed.

The distillative separation affords, at the bottom of the column, a substantially anhydrous mixture of carbonate and alkanol, and, at the top of the column, a carbonate-free mixture of low-boiling alkanols, with or without water and/or polar extractant.

An improvement in the alkanol recovery can be achieved by feeding the low-boiling phase drawn off via the top of the column to a phase separator. In the phase separator, a separation is effected into a phase comprising substantially alkanol and a phase comprising substantially water and/or polar extractant. A further advantage of the use of a phase separator is that the energy requirement for evaporation and condensation is reduced, that the column loading is reduced and also that the carbonate loss is reduced.

The phase which is obtained in the phase separation and comprises substantially alkanol from the phase separator is preferably recycled as reflux into the column. One advantage of recycling the alkanolic phase is that the number of plates is lower than in a column without reflux from the phase separator, and the column height can thus be reduced.

In a further process variant, the condensed vapor stream is fed to a phase separator. In the phase separator, a separation is effected into a substantially organic phase and a substantially polar phase. The substantially organic phase is fed to the distillation column. In the distillation column, a further separation is effected into a bottom product comprising carbonate and alkanol, and also a low-boiling top product comprising alkanol, with or without water and/or polar extractant.

The advantage over the process variant in which the top stream withdrawn from the distillation column is fed to a phase separator is that the amount of feed and the water content in the feed are greatly reduced and it is thus possible to use a column with a smaller column diameter and the energy requirement is reduced.

For continuous distillative separation, particular preference is given to the process variant in which the stream which comprises water and/or polar extractant and low-boiling alkanols and is drawn off via the top of the distillation column is fed to a phase separator. The reflux ratio in the distillation column is preferably in a range between 0.3 and 2.8 kg/kg. The distillation is preferably carried out in a distillation column having from 8 to 18 theoretical plates.

The pressure at which the distillation is carried out is preferably in the range between 0.5 and 2000 mbar, more preferably between 50 and 950 mbar.

In the batchwise distillative separation, in contrast to the continuous distillative separation, there is no collection of the vapor stream, but rather the individual vapor streams or fractions are distilled off sequentially for the concentration by distillation. In this case, the distillation column used may be operated as a pure rectifying column or as a distillation column with rectifying and stripping section.

When the column is operated as a pure rectifying column, the vapor feed is preferably disposed as a side feed in the column bottom. When the distillation column is operated as a pure rectifying column, all fractions are drawn off as distillate one after another. As the first fraction, a mixture of low-boiling alkanol with or without water and/or polar extractant is drawn off as the top product. This mixture is separated in a phase separator into an organic and a polar phase. In a preferred embodiment, the organic phase is subsequently fed back to the top of the column. The polar phase is discharged.

As soon as the amount of the discharged polar phase goes below a predefined value, the distillate is collected in an intermediate vessel. The water concentration or concentration of polar extractant in the distillate which is fed to the intermediate vessel is measured. As soon as the concentration of water or polar extractant goes below a predefined value, the feed to the intermediate vessel is closed and the high-boiling fraction comprising carbonate and high-boiling alkanols is discharged.

When the composition of the distillate stream already has the required composition after the removal of the low-boiling fraction, it will be appreciated that it is possible to dispense with the intermediate vessel and to directly discharge the high-boiling fraction. The advantage of the operation of the distillation column as a pure rectifying column is its low column height.

The advantage of the operation of the distillation column with stripping and rectifying section is the high recovery rate in relation to the carbonates and also a lower energy consumption and a shorter distillation time.

In a preferred embodiment, in the case of operation of the distillation column as a pure rectifying column, the bottoms of the column are fed back into the apparatus in which the organic phase comprising alkoxycarbonylaminotriazine is concentrated by distillation.

The preferred process variant in the batchwise distillative separation is that in which the distillation column is operated as a distillation column with rectifying and stripping section. The advantage of this process variant are the higher recovery rates for carbonates than in the case of operation of the distillation column as a pure rectifying column.

In the case of operation of the distillation column as a distillation column with rectifying and stripping section, the vapor obtained from the spray drier is fed directly as a side feed to a distillation column. Within the distillation column, a separation is effected into a low-boiling and a high-boiling fraction. In the distillative separation, a mixture which comprises low-boiling alkanol and also water and/or polar extractant is initially drawn off in a first forerun as the top product. In a preferred embodiment, the first forerun is separated in a phase separator into an organic and a polar phase. The organic phase is preferably fed as forerun back to the top of the distillation column and the polar phase is discharged.

As soon as the polar phase which has been drawn off goes below a predefined value, the distillate is collected in an intermediate vessel. In a preferred embodiment, the distillate which is collected in the intermediate vessel is not conducted through a phase separator.

As soon as the concentration of water or polar extractant in the distillate goes below a predefined value, the feed to the intermediate vessel is closed and the high-boiling fraction from the bottom of the distillation column is discharged. There is then no longer any reflux into the apparatus in which the organic phase comprising alkoxycarbonylaminotriazine is concentrated.

The reflux ratio is preferably in the range between 0 and 15 kg/kg.

A preferred distillation column in the distillative separation carried out batchwise has between 4 and 10 theoretical plates. The column is, as in the continuous distillative separation too, operated preferably at a pressure in the range from 0.5 to 2000 mbar at the top of the column. More preferably, the pressure is between 50 and 950 mbar.

Via the top of the distillation column, alkanols, if appropriate low boilers and water and/or polar extractant are drawn off. In a particularly preferred embodiment, this stream is subsequently fed to a phase separator in which the polar phase is separated from the organic phase. The organic phase is preferably fed as reflux back to the distillation column at the top thereof.

In a particularly preferred embodiment, the distillation column comprises a side draw arranged preferably in the stripping section, via which a preferably vaporous and substantially anhydrous stream comprising carbonate and alkanol is drawn off. A particularly preferred position of the side draw is directly above the column bottom or directly below the separating internals in the column.

Advantages of this operating mode lie in the recovery of a majority of the carbonates via side draw for reuse in the reaction, the reduction in the carbonate content in the product stream, and in the recovery of anhydrous high-boiling alkanols, for example n-butanol, via the side draw.

In a preferred embodiment, the distillation column comprises from 8 to 22 theoretical plates. The reflux ratio of the organic phase at the top of the column is preferably in the range between 0.2 and 3 kg/kg.

EXAMPLES

Example 1

30 kg/h of a mixture of 50% trialkoxycarbonylaminotriazine and 50% butanol were atomized in a spray tower with a two-substance nozzle having a diameter of 6 mm. The gas used for the atomization was nitrogen with a pressure of 4.5 bar and a mass flow rate of 80 kg/h. The mixture of trialkoxycarbonylaminotriazine and butanol was fed to the two-substance nozzle at ambient pressure. The drying in the spray drier was effected under a nitrogen atmosphere. To this end, the spray drier was operated with 1480 kg/h of nitrogen as cycle gas with a gas inlet temperature of 91° C. and a gas outlet temperature of 76° C. at ambient pressure. In the spray drier, a white powder formed.

Example 2

8 g/min of a mixture of 50% trialkoxycarbonylaminotriazine and 50% butanol were atomized in a spray tower with a two-substance nozzle having a diameter of 0.5 mm. The gas supplied to the two-substance nozzle for atomization was 800 l/h of nitrogen. The spray drier was operated with an elevated pressure of 18 mbar. The drying in the spray drier was effected under a nitrogen atmosphere. To this end, the spray drier was operated with 10 $m^3$/h of nitrogen with a gas inlet temperature of 126° C. and a gas outlet temperature of 73° C. as cycle gas. In the spray drier, a white powder formed.

What is claimed is:

1. A process for preparing free-flowing, pulverulent alkoxycarbonylaminotriazine from an alkanolic reaction mixture, wherein the reaction mixture comprises at least one alkoxycarbonylaminotriazine, at least one cyclic and/or acyclic carbonic ester, at least one $C_1$-$C_{13}$-alkanol which, optionally, comprises one or two oxygen atoms in the form of ether bonds and is, optionally, substituted by $C_1$-$C_4$-alkyl and/or hydroxyl, and also at least one alkali metal alkoxide or alkaline earth metal alkoxide, with or without melamine and with or without catalyst, the process comprising:
   atomizing and drying the reaction mixture in a spray drier, thereby preparing the free-flowing, pulverulent alkoxycarbonylaminotriazine.

2. The process according to claim 1, wherein the spray drying is performed at a temperature in a range from 50 to 250° C. and at ambient pressure or an elevated or reduced pressure of up to +/−0.01 MPa based on the ambient pressure.

3. The process according to claim 1, wherein the spray drying is carried out at a temperature in a range from 70 to 100° C.

4. The process according to claim 1, wherein the pulverulent alkoxycarbonylaminotriazine is removed in a fabric filter or a cyclone.

5. The process according to claim 4, wherein the fabric filter is a candle filter, bag filter or hose filter.

6. The process according to claim 4, wherein the filter material is at least one is selected from the group consisting of polytetrafluoroethylene, silicone, and polyester.

7. The process according to claim 1, wherein the reaction mixture comprising at least one alkoxycarbonylaminotriazine is atomized with the aid of a nitrogen stream.

8. The process according to claim 1, wherein the spray drying is performed in a nitrogen atmosphere.

9. The process according to claim 8, wherein the nitrogen is used as cycle gas.

10. The process according to claim 9, wherein the nitrogen used as cycle gas is purified in a scrubber.

11. The process according to claim 1, wherein the reaction mixture comprising the at least one alkoxycarbonylaminotriazine is worked up, before the spray drying, by neutralizing the mixture, removing ionic and/or polar components by ion exchange and/or extraction, and, optionally, concentrating the mixture.

12. The process according to claim 11, wherein the concentration is carried out before or after the ion exchange or before or after the extraction.

13. The process according to claim 11, wherein the concentration is carried out by an evaporation, distillation, rectification or membrane separation process.

14. The process according to claim 1, wherein a vapor stream obtained in the spray drying and, optionally, a stream which has been depleted in alkoxycarbonylaminotriazine and is obtained in a concentration of the alkoxycarbonylaminotriazine is separated distillatively into an organic and a polar phase.

15. The process according to claim 1, wherein the alkoxycarbonylaminotriazine is represented by the following formula (I):

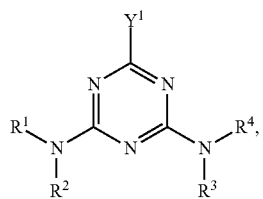

(I)

wherein:

$Y^1$ is hydrogen, $C_1$-$C_4$-alkyl, phenyl optionally substituted by $C_1$-$C_4$-alkyl, $C_1$-$C_4$-alkoxy, or halogen, or a radical of the formula $NR^5R^6$ and each of $R^1$, $R^2$, $R^3$, $R^4$, $R^5$ and $R^6$ is independently hydrogen or a radical of the formula COOX or X, or selected from the group consisting of (—$CH_2$—O)$_1$-H, (—$CH_2$—O)$_1$-R, (—$CH_2$—O)$_k$—$CH_2$—N(Z)-Q, and (—$CH_2$—O)$_k$—$CH_2$—N(Z)—Q, wherein k is from 0 to 10 and l is from 1 to 10, R is selected from the group of consisting of alkyl, cycloalkyl, and alkylaryl, Q is a triazine radical of the formula (II):

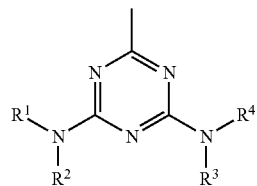

(II)

X is $C_1$-$C_{13}$-alkyl wherein the carbon skeleton may be interrupted by 1 or 2 nonadjacent oxygen atoms in ether function and/or substituted by hydroxyl, or is $C_3$-$C_6$-alkenyl and Z is an $R^1$, $R^2$, $R^3$, $R^4$, $R^5$ or $R^6$ radical as defined above, and at least one of the $R^1$ to $R^4$ radicals or, when $Y^1$ is $NR^5R^6$, at least one of the $R^1$ to $R^6$ radicals, is COOX.

16. The process according to claim 15, wherein the R groups comprise fewer than 13 carbon atoms and is a $C_1$-$C_{13}$-alkyl.

17. The process according to claim 15, wherein the R groups is methyl or butyl.

* * * * *